United States Patent
Meeus et al.

(10) Patent No.: US 9,265,771 B2
(45) Date of Patent: Feb. 23, 2016

(54) METHOD FOR TREATING LYME DISEASE

(71) Applicant: Zoetis Services LLC, Florham Park, NJ (US)

(72) Inventors: Patrick F. M. Meeus, Kalamazoo, MI (US); Christopher L. Haber, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/370,239

(22) PCT Filed: Dec. 20, 2012

(86) PCT No.: PCT/US2012/070753
§ 371 (c)(1),
(2) Date: Jul. 2, 2014

(87) PCT Pub. No.: WO2013/103531
PCT Pub. Date: Jul. 11, 2013

(65) Prior Publication Data
US 2014/0343003 A1  Nov. 20, 2014

(51) Int. Cl.
*A61K 31/546* (2006.01)
*A61K 45/06* (2006.01)
*A61K 31/43* (2006.01)
*A61K 31/65* (2006.01)
*A61K 31/7052* (2006.01)

(52) U.S. Cl.
CPC .............. *A61K 31/546* (2013.01); *A61K 31/43* (2013.01); *A61K 31/65* (2013.01); *A61K 31/7052* (2013.01); *A61K 45/06* (2013.01)

(58) Field of Classification Search
None
See application file for complete search history.

(56) References Cited

FOREIGN PATENT DOCUMENTS

WO   2011/142731   11/2011

OTHER PUBLICATIONS

Pfizer, Freedom of Information Summary, Convenia, Apr. 25, 2008.*
Stegemann, Antimicrobial Agents and Chemotherapy, Jul. 2006, p. 2286-2292.*
AVMA & AAVP Capsules. 2012 AVMA & AAVP Symposia, Aug. 3-7.*
PCT International Search Report, PCT/US2012/070753, mailed Apr. 17, 2013 (4 pages).
"Lyme borreliosis", In: Dawn Merton Boothe: "Small Animal Clinical Pharmacology & Therapeutics", Jan. 1, 2011, Elsevier Saunders, p. 351.
Maddison, "Small Animal Clinical Pharmacology", Jan. 1, 2008, Elsevier, pp. 166-167.
Marques, "Lyme Disease: A Review", Current Allergy and Asthma Reports, 10(1):13-20, 2010.
Wernick and Muntener, "Cefovecin: A New Long-acting Cephalosporin", Journal of Exotic Pet Medicine, 19 (4):317-322, 2010.
Levy et al., "Quantitative Measurement of C6 Antibody following Antibiotic Treatment of Borrelia burgdorferi Antibody-Positive Nonclinical Dogs", Clinical and Vaccine Immunology, 15(1):115-119, 2008.
Littman et al., "ACVIM Small Animal Consensus Statement on Lyme Disease in Dogs: Diagnosis, Treatment, and Prevention", Journal of Veterinary Internal Medicine, 20(2):422-434, 2006.

* cited by examiner

*Primary Examiner* — Layla Bland
(74) *Attorney, Agent, or Firm* — Paul M. Misiak

(57) ABSTRACT

The present invention provides a method for treating Lyme disease and/or a *Borrelia* infection in animals comprising administering to an animal in need thereof a therapeutically effective amount of cefovecin.

5 Claims, 2 Drawing Sheets

METHOD FOR TREATING LYME DISEASE

FIELD OF THE INVENTION

The present invention provides a method for treating *Borrelia* infection and/or Lyme disease (Borreliosis) in animals comprising administering to an animal in need thereof a therapeutically effective amount of cefovecin.

BACKGROUND OF THE INVENTION

Lyme disease (Borreliosis) is an infectious disease caused by the spirochete *Borrelia burgdorferi*, a tick-born bacterium infecting animals (e.g., human, canine, feline, bovine, equine, and birds). Clinical signs are well characterized in canine and include fever, arthritis, anorexia, lymphadenopathy, and glomerulonephritis in some cases. However, most exposed canines remain asymptomatic with only an estimated 5% developing the clinical syndrome called Lyme disease. In equine, clinical signs can include low grade fever, chronic weight loss, sporadic lameness, muscle tenderness, chronically poor performance, arthritis, and diverse orthopedic problems. Lyme disease has been traditionally treated with antibiotics. Current drug treatment regimens can require high doses of antibiotics for long durations of time. Since recommended treatments are of long duration and are not conducive to compliance, and because infections can persist even after prolonged therapy, new treatment strategies for animals, particularly canine and equine, and more particularly, canine, are needed. The present invention overcomes one or more of the various disadvantages of, or improves upon, the properties of existing antibiotic treatments. In particular, the present invention provides a compliant and efficacious treatment choice for Lyme disease.

SUMMARY

The present invention provides a method of treating an animal with a *Borrelia* infection and/or Lyme disease by administering a therapeutically effective amount of cefovecin sodium (i.e., Convenia®) to said animal in need thereof.

In another aspect of the invention, the animal is human. In yet another aspect of the invention, the animal is non-human. Non-human animals include, but are not limited to: canine, feline, equine, bovine, and birds. The preferred non-human animals are canine and equine, and the more preferred non-human animal is canine. Birds include, but are not limited to ducks, geese and chickens.

In another aspect of the invention, cefovecin sodium is administered at least once, and preferably twice to the animal in need thereof. The second cefovecin sodium dose can be administered from about 10 to 13 days after the first dose or as deemed applicable by the practicing clinician.

In another aspect of the invention, the cefovecin sodium is administered by injection. The preferred route of administration is subcutaneous injection. In yet another aspect of the invention, cefovecin sodium is administered to provide a therapeutically effective dose of about 8 mg/kg cefovecin. In yet another aspect of the invention, cefovecin can be administered with a second antibiotic agent. A preferred second antibiotic agent is amoxicillin or doxycycline. The first or second cefovecin dose can be administered subsequent to or concomitantly with the second antibiotic agent. Cefovecin can also be administered prior to the administration of a second antibiotic agent.

DETAILED DESCRIPTION

Figure 1:
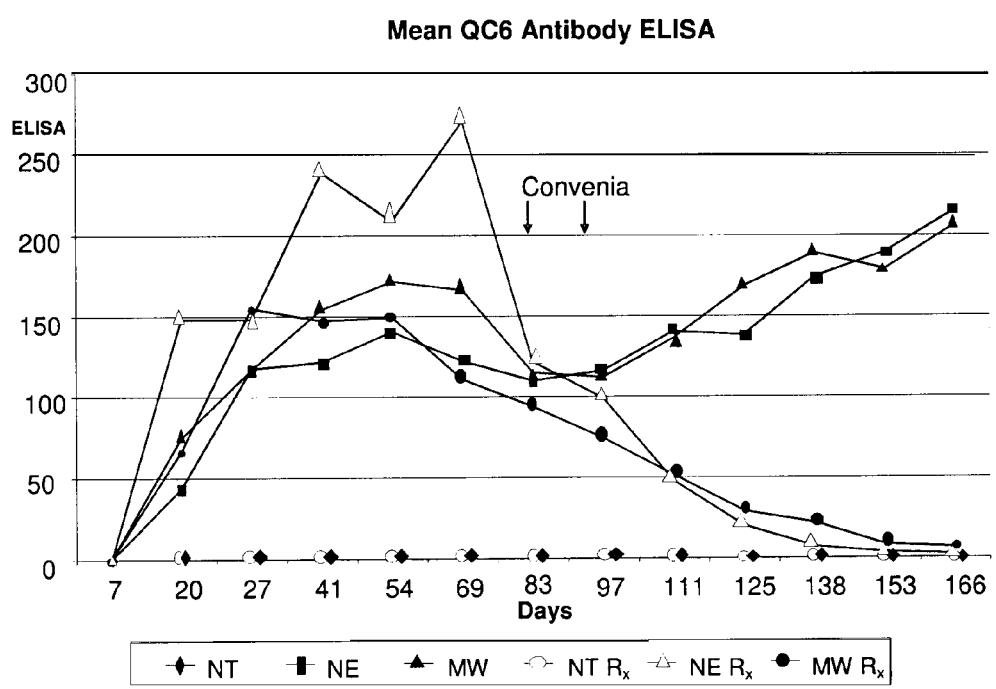
FIG. 1. Mean QC6 antibody ELISA (U/mL). Control dogs (NT, no ticks), dogs challenged with New England (NE) and Midwest (MW) ticks, and Convenia treated=Rx, Days 83 and 97.

It has now surprisingly been found that cefovecin can treat *Borrelia* infection and/or Lyme disease in an animal following an infected tick bite. The studies underlying the present invention demonstrate that the post treatment of an infected animal with cefovecin effectively and unexpectedly treat *Borrelia* infection and Lyme disease with one or two single injectable doses of cefovecin sodium. This finding is particularly important for preventing infection and disease progression and providing a compliance opportunity for the medical (e.g., veterinary) practitioner.

Cefovecin sodium, which is under the trade name Convenia®, is a semi-synthetic broad-spectrum antibacterial of the cephalosporin class. Convenia is designated as (6R,7R)-7-[[(2Z)-(2-amino-4-thiazolyl)(methoxyimino)acetyl]-amino]-8-oxo-3-[(2S)-tetrahydro-2-furanyl]-5-thia-1-azabicyclo[4.2.0]oct-2-ene-2-carboxylic acid, monosodium salt. Cefovecin sodium, cefovecin, Convenia, and Convenia® are herein used interchangeably. In canines and felines, cefovecin is indicated for skin infections (e.g., superficial pyoderma, wounds, and abscesses) and urinary tract infections associated with numerous bacterial strains. When administered, cefovecin is rapidly and completely absorbed following subcutaneous injection. The elimination half-life is about 133- and 166-hours in canine and feline, respectively. The long half-life provides extended antibacterial activity for up to 7 and 14 days against certain bacterial strains. Convenia is presented as a lyophilized pellet that, after reconstitution with 10 mL sterile water for injection, contains 80 mg/mL cefovecin. For the skin and urinary tract infections described above, Convenia is administered as a 0.1 mL/kg (8 mg/kg) subcutaneous injection.

With respect to the above method, and throughout the application and claims, the following terms have the meanings defined herein.

In the context of the present invention "*Borrelia burgdorferi*" encompasses the genospecies complex *Borrelia burgdorferi sensu lato*, particular examples being *B. afzelii*, *B. garinii*, *B. burgdorferi sensu stricto*, *B. valaisiana*, *B. spielmanii*, and *B. lusitaniae*. The present invention in particular relates to *B. burgdorferi sensu stricto*.

In the context of the present invention "Lyme disease" encompasses Lyme disease, borreliosis, and Lyme borreliosis.

In the context of the present invention, "animal(s)", as used herein, encompasses an individual animal that is a mammal or bird. Specifically, mammal refers to a vertebrate animal that is human and non-human, which are members of the taxonomic class Mammalia. Non-exclusive examples of non-human animals include canine, feline, equine, and bovine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which can also be referred to as fowl.

In the context of the present invention, "treatment", "treating", and the like, encompasses the reversal, alleviation, or inhibition of the bacterial infection or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection. Thus, treatment can refer to administration of Convenia to an animal that is not at the time of administration showing clinical signs of infection. In the context of the present invention, "therapeutically effective amount" or the like, as it relates to a drug (e.g., cefovecin sodium), refers to sufficient amounts or delivery rates of a drug which achieves any appreciable level of therapeutic results in treating a condition for which the drug is being delivered. It is understood that "appreciable level of therapeutic results" may or may not meet any government agencies' efficacy standards for approving the commercialization of a product. It is understood that various biological factors may affect the ability of a substance to perform its intended task. Therefore, a "therapeutically effective amount" may be dependent in some instances on such biological factors to some degree. However, for each drug, there is usually a consensus among those skilled in the art on the range of doses that are sufficient in most subjects. Further, while the achievement of therapeutic effects may be measured by a clinician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

Cefovecin can be administered by any route that effectively treats Lyme disease. Suitable administration methods include, but are not limited to, parenteral methods such as intravenous, subcutaneous and intramuscular injection. Subcutaneous injection is the preferred route of administration.

Oral antibiotics are usually the standard course of treatment for Lyme disease and/or Borrelia infection. For example, standard course of treatment include recommended doses of: doxycycline—10 mg/kg twice daily; amoxicillin 20 mg/kg four times daily; azithromycin 25 mg/kg once daily; oxytetracycline 6.6-11 mg/kg once daily for ten days; and minocycline 4 mg/kg once daily. Generally, these antibiotics are administered for a duration of between 30 days to about 60 days. Intravenous antibiotics include, but are not limited to ceftriaxone 25 mg/kg once daily. Antibiotics can be given concomitantly or sequentially to the animal in need thereof. Concomitant administration refers to administration of one agent (e.g., cefovecin) with a second antibiotic agent at about the same time. Sequential administration refers to the administration of one antibiotic (e.g., amoxicillin) and then hours or days later the administration of a second antibiotic, e.g., cefovecin. The alternate sequence of dosing is also contemplated, e.g., where cefovecin is administered first.

EXPERIMENTALS

Three outer surface proteins (Osp) on *B. burgdorferi* are important for diagnosis and prevention, and are expressed by the organism in response to its local environment. OspA is the prevalent surface protein of *B. burgdorferi* in the tick gut and in in-vitro tissue culture; hence its presence in-vivo is attributed to the immune response following vaccination. OspC is the predominant Osp following transmission of *B. burgdorferi* from tick to animal and shows up during the early phase of infection as it is produced by the *Borrelia* spirochete. OspF is another surface protein that is generally observed in late-stage disease. The C in OspC refers to a 25-amino acid, C6 peptide in the sixth invariable region of an outer membrane lipoprotein (VIsE). Antibody against C6 is highly accurate as a serologic diagnosis of Lyme disease independent of a subject's (e.g., canine) vaccination status. Further, the generation of C6 antibodies implies an active infection with viable spirochetes. Serological methods for detecting *B. burgdorferi*/Lyme disease were conducted using the IDEXX qualitative SNAP-4Dx ELISA and the Quantitative C6 (Quant C6 or QC6) diagnostic kits, which are enzyme linked immunosorbent assays against the previously described 25-amino-acid C6 peptide. QC6 ELISA data, units/mL, are useful for guidance in initiating and evaluating response to therapy (See Levy S A, O'Connor T P, Hanscom J L, Shields P, et al. Quantitative measurement of a C6 antibody following antibiotic treatment of *Borrelia burgdorferi* antibody-positive, nonclinical dogs. *Clin Vacc Immunol* 2008; 15(1):115-119 and Littman M P, Goldstein R E, Labato M A, et al. ACVIM Small Animal Concensus Statement on Lyme Disease in Dogs: Diagnosis, Treatment and Prevention. *J Vet Intern Med* 2006; 20: 422-434).

The diagnosis of canine Lyme disease typically involves a four-pronged algorithm based on exposure to ticks likely carrying *Borrelia* (e.g., exposure in an endemic area for Lyme disease), clinical signs, ruling out other differential diseases in the diagnosis, and response to antimicrobial therapy.

In-Vitro Assessment of Cefovecin Efficacy

*B. burgdorferi sensu stricto* (B31 strain) was cultured. The experimental (triplicate) groups included a control, 0.02 µg/mL cefovecin, and 2 µg/mL cefovecin. Cultures were viewed by light microscopy at 0, 6, 24, 30, 48, and 54 hours post inoculation to assess number of live spirochetes (Table 1).

TABLE 1

Number of *B. burgdorferi* spirochetes per field-of-view
(geometric mean per ten field of views)

| Culture Hours | 0 µg/mL | | | 0.02 µg/mL | | | 2 µg/mL | | |
|---|---|---|---|---|---|---|---|---|---|
| | A | B | C | A | B | C | A | B | C |
| 0 | 0 | 0 | 0 | 0 | 0 | 0 | 0 | 0 | 0 |
| 6 | 0 | 0.5 | 0.2 | 0.1 | 0.4 | 0.2 | 0.8 | 0.6 | 0.1 |
| 24 | 1.3 | 1.5 | 2.1 | 1.7 | 2.1 | 2.0 | 0.2 | 0 | 0 |
| 30 | 1.7 | 4.9 | 1.6 | 3.6 | 2.1 | 4.6 | 0 | 0 | 0 |
| 48 | 8.7 | 7.7 | 8.1 | 7.2 | 4.1 | 5.9 | 0 | 0 | 0 |
| 54 | 13.1 | 15.8 | 11.1 | 8.1 | 10.2 | 9.0 | 0 | 0 | 0 |

Cefovecin at a concentration of 2 μg/mL eliminates *B. burgdorferi* in culture after about 24 hours. Further, a cefovecin concentration of 0.02 μg/mL retards growth of *B. burgdorferi* by at least 30% in 54 hours. Following the in-vitro study, two in-vivo studies (Study A and B) were conducted in dogs.

Study A

Twenty-three adult female beagle dogs were used in this study; all were sero-negative for *Borrelia*, not vaccinated with any *Borrelia* spp vaccines, and acclimated at the study facility for seven days prior to any study activities. The study was conducted under National Research Council guidelines (1996. Dogs were randomized to a non-infected control (n=7 dogs) group, or infected groups (n=8 dogs/region) using ticks from two regions of the USA, Region A (New England (NE), i.e., Rhode Island) and Region B (Midwest (MW), i.e., Wisconsin). Dogs were infected on Day 0 with up to 30 *Ixodes scapularis* ticks per dog. Tick attachment was monitored daily and after nine days, remaining ticks were harvested and all dogs were treated with two topical applications of an approved acaricide observing a 30-day interval between applications. Dogs were monitored 21-days post-challenge for pyrexia, and the entire post-challenge period for clinical signs of Lyme disease (lameness, ataxia, anorexia, lymphadenopathy and depression).

Assays: SNAP-4Dx, Quantitative C6 (QC6) ELISA and Skin Biopsy

Blood was collected from each dog weekly to Day 28, then every two-weeks for the remainder of the study (166 days). Serum antibodies to *Borrelia* were assayed using SNAP-4Dx and QC6 ELISA. Two skin punch biopsies were collected near tick attachment sites from each dog every 28 days post-challenge for bacterial culture.

Post-Challenge

Forty-one days after tick infestation, 8 of 16 dogs were positive for *B. burgdorferi* by SNAP-4Dx, and all 16 dogs were SNAP-4Dx positive by Day 83. The QC6 ELISA added sensitivity in detection showing a general increase in antibody levels (infection) 20 days post-tick infestation, or 3 weeks earlier than SNAP-4Dx. Mean QC6 (Table 2) levels increased through Days 54 to 69, then leveled off or declined through Day 83 (FIG. 1). On Days 83 and 97, Convenia was administered (8 mg/kg bodyweight; subcutaneous injection). Treated dogs, 8 *B. burgdorferi*-positive and 4 controls, were compared to untreated cohorts (8 *B. burgdorferi*-positive, and 3 controls). Comparisons included serology, skin culture results and joint pathology.

Results

Other than sporadic, transient single-leg lameness, dogs did not demonstrate clinical signs of Lyme disease such as pyrexia, depression, lameness (sustained, shifting leg) or ataxia. Erythema migrans was not observed.

Bacterial cultures of skin biopsy samples from infected dogs (n=16; 100.0%) yielded spirochetes at 28 days post-challenge. Fifteen and eleven continued as culture-positive 54 and 83 days post-challenge, respectively. Skin samples from non-infected controls were consistently negative for *B. burgdorferi*.

Figure 2:
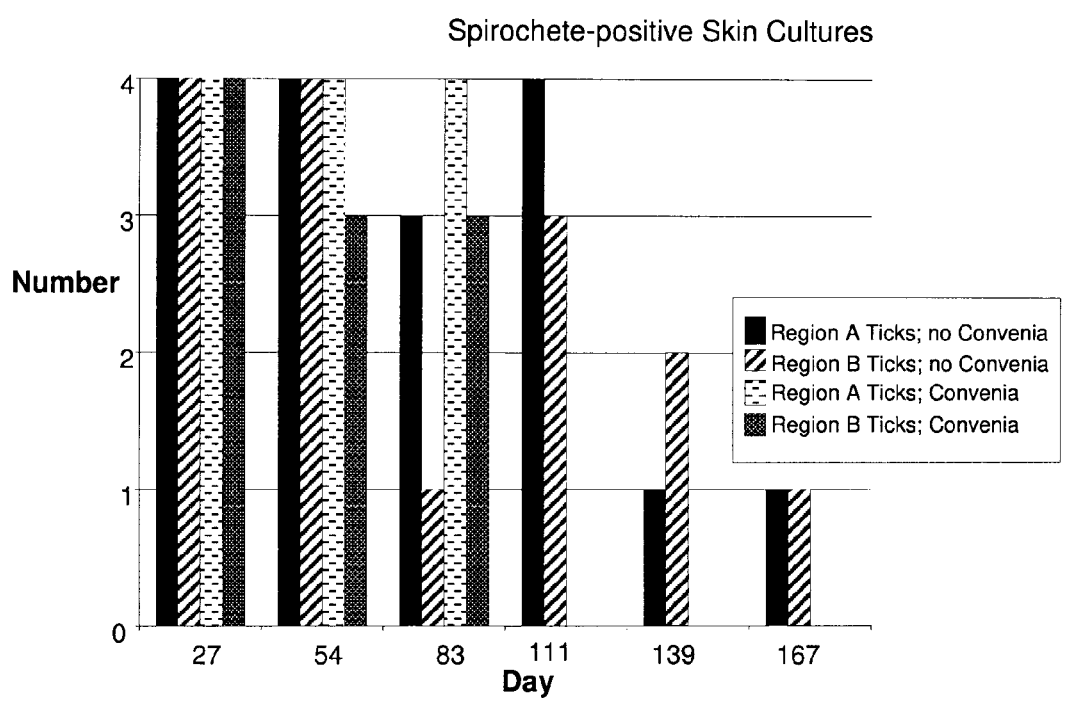
FIG. 2. Number of dogs, 4 per group, culture-positive for spirochetes from skin (Convenia dosed on Days 83 and 97)

Prior to administration of Convenia on Day 83, all dogs in that group (N=8; 100%) were SNAP-4Dx positive for *B. burgdorferi* and five to seven remained positive through the study (Day 166). Infected, untreated dogs (N=8; 100%) were SNAP-4Dx positive from Days 83 to 111; seven (88%) remained positive through Day 166; one dog reverted to SNAP-4Dx negative status on Day 125. All non-infected controls were SNAP-negative for *B. burgdorferi*. No adverse or unexpected events occurred during or following Convenia administration. Mean QC6 antibody ELISA levels in Convenia-treated dogs showed marked declines, starting from a range of 94 to 122 U/mL pretreatment, decreasing to 3 to 6.5 U/mL at the end of the study. Infected, untreated dogs in the same time frame had QC6 antibody levels ranging from 110 to 115 U/mL that increased as the study progressed, ending at levels from 206 to 215 U/mL (FIG. 1). Seven (88%) of eight dogs in the Convenia group were culture-positive for spirochetes from skin prior to treatment; and all were negative on bacterial culture post-treatment (Days 111 to 166). Skin samples from four, seven and two of the eight infected, untreated dogs were culture positive for spirochetes from Days 83 onward (FIG. 2).

Ten joints from each dog were cultured for spirochetes and examined microscopically for changes. Joints included carpus, elbow, shoulder, stifle and tarsus on both the right and left, front and rear limbs. Skin sections were also examined for Lyme disease related changes (pathology). There were six joints from untreated dogs that cultured positive for spirochetes compared to none from dogs treated with Convenia. Microscopically, all untreated, infected dogs had skin sections with inflammatory and other changes as described for Lyme disease, whereas six of eight (75%) treated dogs had similar findings. With the exception of one treated dog with all joints free of pathology, all other dogs had at least two joints showing Lyme disease changes. Despite the microscopic findings, definitively attributing joint pathology to infection or amelioration of pathology as a result of Convenia therapy was equivocal. Dogs in this study were aged (1.2 to 4.6 years of age), with all demonstrating some degree of age related changes as background "noise." In general and with respect to inflammation, joints from untreated dogs were characterized as moderate to marked compared to joints from treated dogs graded none to mild inflammatory changes.

The data collectively support Convenia therapy in reducing the inflammatory component of Lyme disease, markedly reducing circulating QC6 antibodies to *Borrelia*, and ablating live spirochetes in the skin as harvested near tick attachments.

TABLE 2

Mean QC6 Antibody Levels (U/mL) × Day

| | | Untreated | | | Convenia Rx Days 83 and 97 | | |
| --- | --- | --- | --- | --- | --- | --- | --- |
| | | | Group | | | | |
| Day | 1 Control | 2 NE Ticks | 3 MW Ticks | 4 Control | 5 NE Ticks | 6 MW Ticks | Event |
| 0 | 0 | 0 | 0 | 0 | 0 | 0 | Ixodes infestation |
| 7 | 0 | 0 | 0 | 0 | 0 | 0 | |
| 20 | 0 | 43.75 | 74.75 | 0 | 148.5 | 66.5 | |
| 27 | 0 | 117.25 | 116.75 | 0 | 148.75 | 155 | |
| 41 | 0 | 121.5 | 154.5 | 0 | 239.25 | 147.25 | |

TABLE 2-continued

Mean QC6 Antibody Levels (U/mL) × Day

| | Untreated | | | Convenia Rx Days 83 and 97 | | |
|---|---|---|---|---|---|---|
| | | Group | | | | |
| Day | 1 Control | 2 NE Ticks | 3 MW Ticks | 4 Control | 5 NE Ticks | 6 MW Ticks | Event |
| 54 | 0 | 140.5 | 171.75 | 0 | 209.5 | 149.25 | |
| 69 | 0 | 122 | 166.25 | 0 | 270.75 | 110.75 | |
| 83 | 0 | 109.75 | 114.75 | 0 | 122 | 93.75 | Convenia |
| 97 | 0 | 116 | 112 | 0 | 99.5 | 74.25 | Convenia |
| 111 | 0 | 140.5 | 136.25 | 0 | 48.25 | 51.5 | |
| 125 | 0 | 138.25 | 168.75 | 0 | 20.5 | 29 | |
| 138 | 0 | 174.25 | 189 | 0 | 7.75 | 22 | |
| 153 | 0 | 189.5 | 179 | 0 | 4.25 | 8.25 | |
| 166 | 0 | 215.25 | 206.25 | 0 | 3 | 6.5 | |

Study B

Thirty-two (18 male and 14 female) beagle dogs were sero-negative for *Borrelia burgdorferi*, not vaccinated with any *Borrelia* spp vaccines, and acclimated at the study facility for seven days. The study was conducted under National Research Council guidelines (1996). Dogs were randomly allotted to four groups, 8 dogs each: untreated controls (T01), and three groups administered antibiotics: doxycycline (T02), amoxicillin (T03) and Convenia (T04). Field-caught *Ixodes* from the northeast USA were placed on the dogs without containment chambers for 10 days; after ticks fed to repletion, dogs were treated with two applications of an approved topical acaricide with a 30-day interval between applications.

Assays: Serology and Skin Biopsy (Culture and PCR)

Forty days post-challenge, and prior to antibiotic treatments, blood was collected from each dog as were two skin biopsy punch samples near tick attachment sites. Blood was collected approximately monthly post-treatment. Skin biopsies were taken near the tick attachment site on Days 48/49, 118, 146, 180, and 315. Serum antibodies to *Borrelia* were assayed using the IDEXX SNAP-4Dx and QC6 ELISA. In cooperation with Cornell University, serum samples were analyzed using fluorescent-bead-based multiplex assays detecting antibodies against *B. burgdorferi* outer surface proteins OspA, OspC, and OspF. Data were expressed as median fluorescent intensities (MFI), and shown to be specific and sensitive to provide interpretative guidelines regarding infection. The skin biopsies were collected for a polymerase chain reaction (PCR; FlaB) assay and cultured for spirochete detection. At the end of the study, blood and skin biopsies were collected and synovial tissue from the joints were harvested at necropsy.

Antibiotic Regimens

On Day 75 and Day 89 Convenia was administered to the eight dogs in T04 (8 mg/kg bodyweight; subcutaneous injection). The other treated groups received their respective regimens daily and orally for 30 days from Days 75 to 104. Dogs in T02 received doxycycline (10 mg/kg; once daily (SID)) and dogs in T03 received amoxicillin (20 mg/kg; three times daily (TID)). Dogs in T01 served as infected, untreated, controls. Inter-treatment comparisons to evaluate antibiotic efficacy included clinical signs, serology, culture results and pathology.

Results

Thirty of 32 dogs were positive for *B. burgdorferi* infection based on consecutive SNAP-4Dx and PCR and skin biopsy culture results: eight dogs in each of the control and Convenia groups, and seven dogs in each of the amoxicillin and doxycycline groups. Infection monitoring was performed on Days 111, 145, 179, 221, 251, 281, and 314. All dogs assigned to receive an antibiotic were treated per protocol; however there were two dogs, one in each of the doxycycline and amoxicillin groups, that were both SNAP-4Dx and PCR negative for the entire study. In the untreated controls, 62% to 100% of the dogs were SNAP-4Dx positive from Days 48 to 314; whereas SNAP-4Dx positive dogs in groups treated with doxycycline, amoxicillin and Convenia numbered 1, 2, and 2 respectively on Day 179, with none positive for the rest of the study after Day 179 (Table 3).

Prior to infection, all groups demonstrated a mean value<10 U/mL in the QC6 ELISA; a level≥30 U/mL in this assay is considered positive warranting treatment for Lyme disease. One-half to 75% of the control group was above threshold through Day 314, compared to none in any treated groups after Day 111 (Table 4).

Multiplex assay results agreed with interpretive guidelines used to classify *B. burgdorferi* infection as negative, equivocal or positive (Table 5). All dogs, not vaccinated against *B. burgdorferi*, had antibody-OspA values that were consistent with published results for non-vaccinated dogs. Each group had four dogs above threshold for antibody-OspC post-infection, pretreatment (Day 48). One to two dogs in the untreated group remained above infected threshold (antibody-OspC) through the entire study compared to: one dog in T02, Day 221; one in T03, Day 281; and one in T04, Day 111. Six controls (75%) had antibody-OspF levels above threshold from Day 111 to Day 314 (Table 6). In contrast two dogs treated with doxycycline were above infected threshold, one dog on Day 48 and one dog on Day 111; three dogs treated with amoxicillin were above infected threshold on Day 111 (all dogs negative thereafter); and there were two dogs treated with Convenia above infected threshold on Day 48 (all dogs negative thereafter).

At necropsy ten joints were harvested per each dog, formalin-fixed, stained and examined microscopically. Joints included the carpus, elbow, shoulder, stifle and tarsus on both the right and left limbs. Further, a section of skin near tick attachment sites was evaluated from each dog. There were two dogs in the Convenia group (25%) with tissues showing changes as described for Lyme disease, compared to seven controls (87.5%) and three (37.5%) to four (50.0%) dogs in the other antibiotic-treated groups (Table 7). Of the 80 joints evaluated per group, 36 had characteristic Lyme disease changes in the controls, compared to 6, 11 and 12 affected joints in antibiotic-treated groups (Convenia, doxycycline, and amoxicillin, respectively; Table 8). The Convenia group had the lowest incidence of joint changes with six affected of 80.

TABLE 3

SNAP-4Dx Positives by Day of Study (N = 8/group)

| Day of Study | Number of Dogs Group: T01 | T02 | T03 | T04 |
|---|---|---|---|---|
| −15 | 0 | 0 | 0 | 0 |
| 48 | 7 | 6 | 5 | 6 |
| 111 | 8 | 7 | 7 | 5 |
| 145 | 7 | 6 | 3 | 1 |
| 179 | 5 | 1 | 2 | 2 |
| 221 | 6 | 0 | 0 | 0 |
| 251 | 6 | 0 | 0 | 0 |
| 281 | 5 | 0 | 0 | 0 |
| 315 | 6 | 0 | 0 | 0 |

TABLE 4

**Number of Dogs Sero-converted to *B. burgdorferi* per QC6 ELISA (≥30 U/mL = *B. burgdorferi*-positive; IDEXX)**

| Day | T01 No. (%) | T02 No. (%) | T03 No. (%) | T04 No. (%) |
|---|---|---|---|---|
| 48 | 7 (87.5) | 6 (75.0) | 8 (100.0) | 6 (75.0) |
| 111 | 6 (75.0) | 5 (62.5) | 6 (75.0) | 6 (75.0) |
| 145 | 6 (75.0) | 0 (0.0) | 0 (0.0) | 0 (0.0) |
| 179 | 4 (50.0) | 0 (0.0) | 0 (0.0) | 0 (0.0) |
| 221 | 5 (62.5) | 0 (0.0) | 0 (0.0) | 0 (0.0) |
| 251 | 5 (62.5) | 0 (0.0) | 0 (0.0) | 0 (0.0) |
| 281 | 5 (62.5) | 0 (0.0) | 0 (0.0) | 0 (0.0) |
| 314 | 5 (62.5) | 0 (0.0) | 0 (0.0) | 0 (0.0) |

TABLE 5

**Multiplex Assays: Antibodies against Osp A, C, F in *B. burgdorferi* infected Dogs (units: Median Fluorescent Intensity = MFI)**

| Osp | Negative | Equivocal | Positive | Sensitivity % | Specificity % |
|---|---|---|---|---|---|
| A | <500 MFI | ≥500-1000 MFI | ≥1000 MFI | 83 | 90 |
| C | <250 | ≥250-1000 | ≥1000 | 62 | 89 |
| F | <750 | ≥750-1500 | ≥1500 | 82 | 86 |

TABLE 6

Multiplex Assay OspF: MFI Mean by Day; No. Dogs > Positive Threshold by Day (Days −15 to 145)

| Group | Day | −15 | 48 | 111 | 145 |
|---|---|---|---|---|---|
| T01 | Mean: | 226.25 | 995.50 | 3906.13 | 3902.50 |
| | # dogs > 1500 | 0 | 1 | 6 | 6 |
| T02 | Mean: | 113.50 | 943.38 | 1174.38 | 490.63 |
| | # dogs > 1500 | 0 | 1 | 1 | 0 |
| T03 | Mean: | 133.38 | 1083.75 | 1250.25 | 458.13 |
| | # dogs > 1500 | 0 | 2 | 3 | 0 |
| T04 | Mean: | 101.50 | 922.75 | 704.13 | 306.75 |
| | # dogs > 1500 | 0 | 2 | 0 | 0 |

Days 179 to 314

| Group | Day | 179 | 221 | 251 | 281 | 314 |
|---|---|---|---|---|---|---|
| T01 | Mean: | 3520.38 | 3243.38 | 4700.88 | 4825.25 | 4227.13 |
| | # dogs > 1500 | 6 | 6 | 6 | 6 | 6 |
| T02 | Mean: | 395.88 | 334.75 | 340.88 | 343.63 | 353.25 |
| | # dogs > 1500 | 0 | 0 | 0 | 0 | 0 |
| T03 | Mean: | 327.88 | 269.63 | 288.63 | 288.88 | 278.25 |
| | # dogs > 1500 | 0 | 0 | 0 | 0 | 0 |
| T04 | Mean: | 270.00 | 227.13 | 221.88 | 225.63 | 239.88 |
| | # dogs > 1500 | 0 | 0 | 0 | 0 | 0 |

TABLE 7

Number of Dogs with Tissue Changes Described for Lyme Disease in (joints, skin; 8 dogs/group)

| Group | No Tissue Changes # Dogs | % | Tissue Changes # Dogs | % |
|---|---|---|---|---|
| T01 | 1 | 12.5 | 7 | 87.5 |
| T02 | 5 | 62.5 | 3 | 37.5 |
| T03 | 4 | 50 | 4 | 50 |
| T04 | 6 | 75 | 2 | 25 |

TABLE 8

Number of Joints with Changes as Described for Lyme disease (N = 8 each; 80 total/group)

| Group | Carpus R | L | Elbow R | L | Shoulder R | L | Stifle R | L | Tarsus R | L | Cumulative |
|---|---|---|---|---|---|---|---|---|---|---|---|
| T01 | 6 | 7 | 5 | 2 | 3 | 3 | 3 | 4 | 2 | 1 | 36 |
| T02 | 2 | 1 | 1 | 1 | 0 | 1 | 2 | 1 | 0 | 2 | 11 |
| 103 | 2 | 2 | 1 | 1 | 1 | 0 | 2 | 1 | 1 | 1 | 12 |
| T04 | 1 | 1 | 1 | 0 | 0 | 0 | 2 | 1 | 0 | 0 | 6 |

CONCLUSION

Transmission of *Borrelia* from wild-caught *Ixodes* was successful in a controlled environment using the natural route of transmission. Conventional serological assays and bacterial recovery or PCR procedures were used to confirm spirochete transmission. Overall, dogs infected with *B. burgdorferi* and then treated with Convenia demonstrated a clinically relevant reduction in circulating antibodies against Osp of the organism, had no recoverable spirochetes from skin sections, and demonstrated an overall lower grade of inflammation in skin and joints, compared to untreated dogs. Confirming initial study results and comparing Convenia to two, 30-day oral antibiotic regimens, Convenia administered at label dose and interval was not different than either doxycycline or amoxicillin. Infection and efficacy were monitored using SNAP-4Dx, QC6 ELISA, and a recently published multiplex assay shown to be both sensitive and specific. Further and used to definitively confirm Lyme disease infection, microscopic evaluations of articular joints support that antibiotic therapy (oral, injectable) reduced the incidence of lesions, and in dogs receiving Convenia the reduction was 2-fold lower than dogs administered doxycycline or amoxicillin orally for 30 days.

We claim:

1. A method for treating Lyme disease in a canine animal comprising administering to said canine animal in need thereof a therapeutically effective amount of cefovecin sodium.

2. The method of claim 1 wherein cefovecin sodium is administered at least twice to the canine animal in need thereof.

3. The method of claim 2 wherein the second dose of cefovecin sodium is administered about 10 to 13 days after the first dose of cefovecin sodium.

4. The method of claim 1 wherein cefovecin sodium is administered by subcutaneous injection.

5. The method of claim 1 wherein the therapeutically effective amount of cefovecin sodium is about 8 mg/kg bodyweight of cefovecin.

* * * * *